United States Patent [19]

Chen et al.

[11] Patent Number: 5,061,262
[45] Date of Patent: Oct. 29, 1991

[54] HOT MELT ADHESIVE FOR POLYETHYLENE FILM REINFORCEMENT

[75] Inventors: Franklin M. C. Chen; Paul M. Linker, both of Appleton; William R. Van Bemmel, Menasha; Dave A. Soerens, Neenah, all of Wis.

[73] Assignee: Kimberly-Clark Corporation, Neenah, Wis.

[21] Appl. No.: 53,211

[22] Filed: May 21, 1987

[51] Int. Cl.$^5$ ............................................. A61F 13/15
[52] U.S. Cl. .................................................. 604/389
[58] Field of Search ....................... 604/385.1, 389, 390

[56] References Cited

U.S. PATENT DOCUMENTS 3,867,940  2/1975  Mesek et al. .
4,055,182 10/1977  Mack .
4,210,144  7/1980  Sarge, III et al. .
4,296,750 10/1981  Woon et al. .

FOREIGN PATENT DOCUMENTS 0080647  6/1983  European Pat. Off. .
2129689  5/1984  United Kingdom .
2135568  9/1984  United Kingdom .

OTHER PUBLICATIONS

Skeist, *Handbook of Adhesives*, 2nd Ed., 1977, Chapter 29-30, pp. 484-506.

*Primary Examiner*—G. Fred Rosenbaum
*Assistant Examiner*—Sharon Finkel
*Attorney, Agent, or Firm*—Paul Yee

[57] ABSTRACT

An article having a refastenable tape system comprising a flexible substrate having a tear strength, and an adhesive tape member having a peel adhesion value which is greater than the tear strength of the substrate when the tape member is adhered to a first major surface of the substrate. A reinforcement layer composed of a hot melt adhesive is bonded to a second major surface of the substrate located opposite to the first major surface. The reinforcement layer exhibits an elongation-at-break of at least about 100%. The substrate and the reinforcement layer thereby provide a composite tear strength greater than the peel adhesion value of the tape member, and provide a composite elongation-at-break of at least about 100%.

20 Claims, 2 Drawing Sheets

A = 1 in
B = 4 in
C = 6 in

HOT MELT ADHESIVE FOR POLYETHYLENE FILM REINFORCEMENT

TECHNICAL FIELD

The present invention relates to the reinforcement of a selected substrate to provide thereof. More particularly, the present invention relates to the reinforcement of a selected layer of a garment to provide a reinforced target or landing zone for refastenable adhesive tape tabs.

BACKGROUND OF THE INVENTION

Limited use garments, such as disposable gowns and disposable diapers, have often employed refastenable adhesive tapes to secure the garment on the wearer. For example, with disposable diapers, adhesive tape tabs have been employed to secure the waistband portions of the garment about the waist of an infant.

It has been desirable to provide a refastenable tape tab system in which the tape tab can be peeled away and readhered several times to the tape attachment zone. Such operation, however, typically tears the outer layer of the garment. As a result, various techniques have been employed to reinforce selected landing zone regions against which the adhesive tape tab can be repeatedly adhered, removed and readhered.

Certain conventional techniques have employed a separate layer of polymer sheet material bonded to the outer cover sheet of a disposable diaper. For example, see U. K. patent application GB 2 129 689 A published May 23, 1984 with L. Widlund as inventor; European Patent Application EP 0 080 647 A1 published June 8, 1983 with R. de Jonckheere, et al. as inventors; and U. K. patent application GB 2 135 568 A published Sept. 5, 1984 with J. Pasinato, et al. as inventors.

Other diaper structures have reinforced the backsheet material with a flexible structural material, such as scrim, to prevent stretching and rupture of the backsheet due to tension imparted by fastening tape tabs during diapering, wearing of the diaper and removal of the diaper from the infant. For example, see U.S. Pat. No. 3,867,940 issued Feb. 25, 1975 to F. Mesek, et al.

Still other structures have employed a refastenable tape system in which the outer cover of a garment is reinforced with a pattern of adhesive. For example, U.S. Pat. No. 4,210,144 issued July 1, 1980 to H. Sarge III, et al. reinforces the backsheet by coating it with a material having a high tensile strength and a low elongation tensile force property relative to the backsheet material. U.S. Pat. No. 4,296,750 issued Oct. 27, 1981 to L. S. Woon, et al. reinforces the backsheet of a garment with a layer of hot melt adhesive to provide strengthened tape securement zones. The hot melt adhesive layer has a lower modulus of elasticity than the film and is applied in a heat softened condition.

Conventional refastenable tape systems, such as those described in the above documents, have not been completely satisfactory. Those systems which employ separate sheet layers of plastic film or scrim material bonded to the garment outer cover can require complicated and costly manufacturing equipment and processes. The systems which employ patterns of hot melt adhesive bonded to the garment outer cover have not been able to withstand the peel forces generated when a user rapidly peels the fastening tape from adhesive contact with the garment outer cover. The rapid peeling speed normally employed by an ordinary user generates large tensile stresses which can fracture the coating of reinforcement adhesive and tear the garment outer cover.

BRIEF DESCRIPTION OF THE INVENTION

The present invention provides a distinctive article having a refastenable tape system which includes a reinforced, target fastening zone. Generally stated, the article includes a flexible substrate having a tear strength, and an adhesive tape member having a peel adhesion value which is greater than the tear strength of the substrate when the tape member is adhered to a first major surface of the substrate. A reinforcement layer composed of a hot melt adhesive is bonded to a second major surface of the substrate. The second major surface is located opposite to the first major surface, and the reinforcement layer exhibits an elongation-at-break of at least about 100%. The substrate and the reinforcement layer thereby provide a composite tear strength greater than the peel adhesion value of the tape member, and provide a composite elongation-at-break of at least about 100%, as measured at a strain rate of at least about 3 cm/cm/sec.

The article of the invention includes a distinctive reinforced tape attachment zone which advantageously is capable of stretching and deforming to accommodate the strain induced by rapidly peeling an adhered tape member from its adhesive contact with the attachment target zone located on the substrate of the article. As a result of its increased toughness, the attachment target zone is less susceptible to tearing and can more reliably retain its structural integrity and effectiveness in a refastenable tape system.

BRIEF DESCRIPTION OF THE DRAWINGS

The present invention will be more fully understood and further advantages will become apparent when reference is made of the following detailed description of the invention and the drawings, in which.

DETAILED DESCRIPTION OF THE INVENTION

The following detailed description of the invention will be made in the context of a disposable absorbent article, such as a disposable diaper. It will, however, be readily apparent to a person having ordinary skill in the art that the structures of the present invention could also be employed with other articles, such as caps, gowns, aprons, feminine care articles, incontinence garments and the like.

Figure 1:
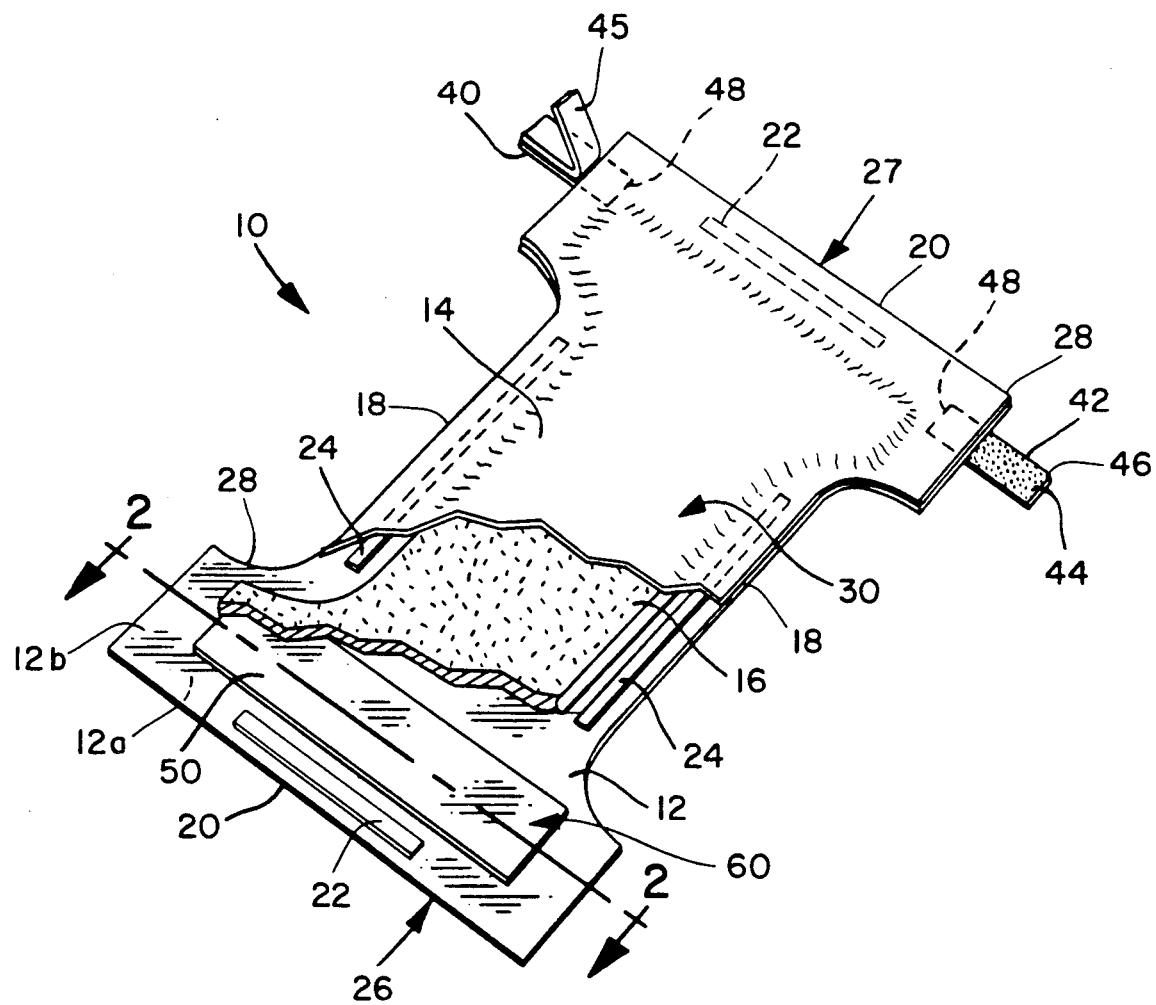
FIG. 1 representatively shows a plan view of a disposable diaper article having a refastenable tape system.
Figure 2:
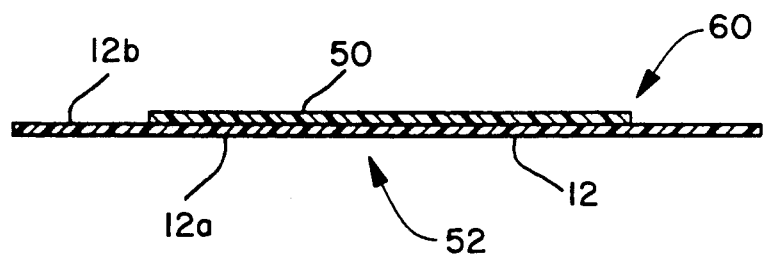
FIG. 2 representatively shows a cross-sectional view taken along line 2—2 of FIG. 1.
Figure 3:
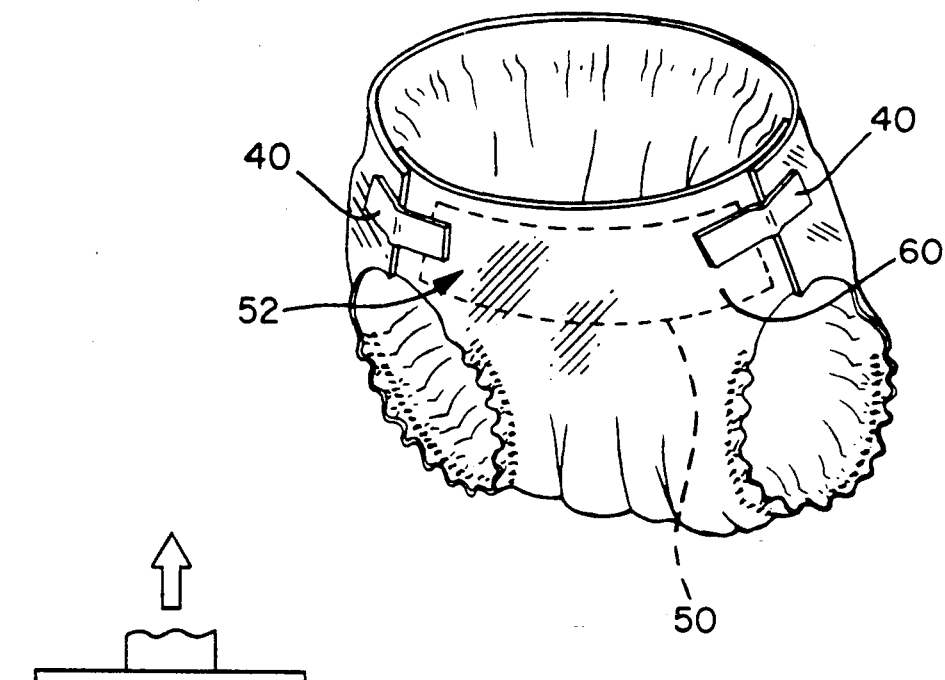
FIG. 3 representatively shows a perspective view of a diaper when worn by an infant.

With reference to FIG. 1, a representative article of the invention comprises a flexible substrate member, such as backsheet 12, which has a selected tear strength. The backsheet forms the outer cover layer of a garment article, and includes a first major surface 12a on an outer side thereof and a second major surface 12b located on an inner side thereof. One or more adhesive tape members 40 are factory bonded to backsheet 12 and have a peel adhesion value which is greater than the tear strength of the backsheet when tape member 40 is adhered to the first major surface of backsheet 12. A reinforcement layer 50 composed of a hot melt adhesive is bonded to the second major surface 12b of the backsheet, which is located opposite the first major surface 12a. In addition, the material comprising reinforcement layer 50 exhibits an elongation-at-break of at least about 100%. The combination of backsheet 12 and reinforcement layer 50 thereby provides a composite tear strength greater than the peel adhesion value of tape member 40, and provides a composite elongation-at-break of at least about 100% when the elongation-at-break value is measured at a strain rate of at least about 3 cm/cm/sec. As a result, the reinforced backsheet composite can withstand the stresses generated by peeling the adhesive tape tab from adhesive contact therewith, and can allow the tape tab to be peeled away substantially without tearing the backsheet.

In a particular aspect of the invention, backsheet 12 is composed of a liquid-impermeable material and defines a front waistband portion 26, a back waistband portion 27 and an intermediate portion 30 interconnecting the front and back waistband portions. A liquid permeable topsheet layer 14 is located in facing relation with the backsheet, and an absorbent body 16 is located between the backsheet and topsheet. An adhesive member 40 is connected with a factory bond to each of two side sections 28 of the back waistband portion of backsheet 12. A user bond portion 46 of the adhesive tape member has a peel adhesion value which is greater than the tear strength of backsheet 12 when tape member 40 is adhered to the first major surface of the backsheet.

In another aspect of the invention, the hot melt adhesive comprising reinforcement layer 50 is composed of a material consisting essentially of about 5-25 wt % of a first ethylene-vinyl acetate copolymer containing about 18-40 wt % vinyl acetate and having a melt index of less than about 100; about 25-45 wt % of a second ethylene-vinyl acetate copolymer containing about 14-20 wt % vinyl acetate and having a melt index of greater than about 400; about 30-40 wt % of tackifier material; and about 10-20 wt % of a paraffin or microcrystalline wax having a needle penetration value of less than about 15 and having a melting point within a temperature range of about 70°-100° C. It should be understood that the description of the above-mentioned composition of reinforcement layer 50 includes the proviso that the constituent components of the reinforcement layer total 100 wt %.

In the illustrated embodiment, backsheet 12 and topsheet 14 are essentially coterminous and extend out past the edges of absorbent body 16 to form marginal edges 18 and 20. The backsheet, topsheet and absorbent body each have waistband portions interconnected by an intermediate portion, and the intermediate portion is narrower than the waistband portions. Diaper 10 thus has a generally hourglass or I-shape planform with the waistband portions 26 and 27 defining ear sections 28 extending along the lateral cross-wise direction of the diaper. The shown embodiment further includes leg elastic members 24, which are attached to each of the diaper side margins 18 and configured to gather and shir the legband portions of diaper 10 to form seals or gaskets about the legs of a wearer. In addition, diaper 10 can include waist elastic members 22 secured to one or more end margins 20 to gather and shir the waistband portions of the diaper.

The various components of diaper 10 are assembled together employing conventional techniques. For example, the components may be attached to one another employing thermal or sonic bonds, or mechanical fasteners, such as snaps or clips. Alternatively, the components can be attached with adhesives, such as hot melt pressure-sensitive adhesives. The adhesives can be applied by employing conventional techniques, such as by spraying adhesive droplets or filaments. In the shown embodiment of the invention, the diaper components are assembled together employing a plurality of generally parallel lines of hot melt pressure-sensitive adhesive oriented along the length dimension of the diaper. In a particular embodiment of the invention, backsheet 12 is composed of a liquid-impermeable material, such as a polymer film. For example, backsheet 12 can be composed of a polyolefin film, such as polyethylene or polypropylene. In another embodiment of the invention, backsheet 12 can be composed of a liquid-impermeable but vapor-permeable material, such as a "breathable", microporous polyethylene film.

Topsheet 14 is typically composed of a liquid-permeable, substantially hydrophobic material, such as a spun-bonded web composed of a synthetic polymer filaments. Alternatively, topsheet 14 may comprise a melt-blown web or a bonded-carded-web composed of synthetic polymer filaments. Suitable synthetic polymers include, for example, polyethylene, polypropylene and polyesters. The topsheet has a pore size that readily allows the passage therethrough of liquids, such as urine and other body exudates. Optionally, the topsheet can be treated with a surfactant, or selectively embossed or perforated with discrete slits or holes extending therethrough.

Absorbent body 16 typically comprises a pad composed of airlaid cellulosic fibers commonly referred as wood pulp fluff. Conventional pads can have a density ranging from about 0.05-0.2 g/cc, and are sufficiently flexible to readily conform to the body of the wearer. Absorbent body 16 may also comprise a coform material composed of a mixture of cellulosic fibers and synthetic polymer fibers. For example, the coform material may comprise an airlaid blend of cellulosic wood pulp fibers and meltblown polyolefin fibers, such as polyethylene and polypropylene fibers.

Absorbent body 16 may also include an effective amount of an inorganic or organic high-absorbency material to enhance the absorptive capacity of the absorbent body. For example, absorbent body 16 can include about 5-95 wt % high-absorbency material, and preferably includes about 10-25 wt % of the high-absorbency material to provide more efficient performance. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers can include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacylamides, polyvinyl pyridine and the like. Other suitable polymers may include hydrolyzed acrylonitrile grafted starch, acrylic acid grafted starch and isobutylene maleic anhydride copolymers, and mixtures thereof. The hydrogel polymers are preferably lightly cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Celanese Corporation, Allied-Colloid, and Stockhausen. Typically, the high-absorbency material is capable of absorbing at least about 15 times its weight in water, and preferably is capable of absorbing at least about 25–50 times its weight in water.

The high-absorbency material can be distributed or otherwise incorporated into absorbent body 16 employing various techniques. For example, the high-absorbency material can be substantially uniformly distributed in the fibers comprising the absorbent body. The material can also be nonuniformly distributed within the fibers to form a generally continuous gradient with either an increasing or decreasing concentration of high-absorbency material. The increasing or decreasing nature of the concentration gradient is determined by observing the concentration moving from the body side of absorbent body 16 to the outer side of the absorbent body. In an alternative arrangement, the high-absorbency material can comprise a discrete layer separate from the fibrous material of absorbent body 16, or can comprise a discrete layer integral with the absorbent body.

Absorbent body 16 can optionally include a tissue wrap 32 to help maintain the integrity of the airlaid fibrous structure. The tissue wrap typically comprises a cellulosic material, such as creped wadding or a high wet-strength tissue.

Backsheet 12 is ordinarily composed of a thin material measuring less than about 0.005 cm in thickness. Preferably, the thickness of backsheet 12 is within the range of about 0.0025–0.0043 cm. In the shown embodiment, backsheet 12 is also embossed or otherwise textured to provide a nonglossy, matte finish. The matte finish material is softer to the touch, provides a more garment-like appearance and produces less rattling noise when manipulated. Backsheet 12 typically has a tensile strength of about 16 MPa (2300 psi) and an extensibility capable of providing an elongation-at-break of about 500%.

The illustrated embodiment of diaper 10 incorporates tape members comprising adhesive tape tabs 40. The tape tab includes a carrier member 42 and an adhesive layer 44 applied and bonded to a major surface of the carrier member. A factory bond section 48 of tape tab 40 is suitably attached to backsheet 12, such as by employing an adhesive bond. A release layer 45 typically covers the adhesive on a user bond section 46 of the tape tab. This release layer is removed by the user prior to use to expose the adhesive on the user bond section. Suitable tape tab materials are available from various vendors, such as 3M Company located in St. Paul, Minn., and Fasson Co. located in Painesville, Ohio.

When diaper 10 is worn by an infant, the waistband sections 26 and 27 of the diaper encircle the infant's waist, and intermediate section 30 extends between the infant's legs and over the infant's crotch area. Tape tabs 40 are then employed to connect the back waistband portion to the front waistband portion and secure the garment on the infant.

When the diaper is first fitted onto the infant, it has been desirable to reposition tape tabs 40 on the front waistband section of diaper 10 to provide a more secure or more comfortable fit. More particularly, it has been desirable to be able to peel tape tab 40 from adhesive contact with backsheet 12, reposition the tape tab and refasten the tab to another portion of backsheet 12. Thereafter during use, it has been desirable to check the diaper for wetness and for any other soiled condition. The user is better able to examine the diaper condition if the tape tabs can be releasably peeled from their adhesive bond with backsheet 12 to allow a further opening of the diaper. If the diaper is not soiled, it is potentially reusable provided the diaper can be resecured about the infant. The process of peeling tape tab 40 from backsheet 12, however, ordinarily tears the backsheet material and destroys its liquid barrier function. In addition, pieces of backsheet material can remain adhered to the tape tab and render it unserviceable. The contamination produced by the residual backsheet material on the tape tab degrades the ability of the tab to refasten onto backsheet 12.

To strengthen and reinforce a selected tape attachment target zone 52 on backsheet 12, reinforcement layer 50 is attached to the inner surface of the backsheet. Thusly configured, reinforcement layer 50 underlies backsheet 12 and is connected to a backsheet surface located opposite to the backsheet surface contacted by tape tab 40.

Persons operating tape tabs 40 ordinarily remove the tape tabs from backsheet 12 at a relatively rapid peel rate of at least about 18 cm/sec. Such a rapid peel rate can provide an impact-type load which effectively multiplies the stress applied to the backsheet, and as a result, the backsheet material becomes more susceptible to tearing. More particularly, at the rapid peel rate described above, tape tab 40 exhibits a peel adhesion value which exceeds the tensile tear strength of backsheet 12.

For the purposes of the present invention, a suitable technique for determining the desired relationship between the tape peel adhesion value and the tear strength of the adhered substrate is the following Refastenability Test:

The tape refastenability test can provide a comparison between the peel adhesion value of the fastening tape and the tear strength of the substrate to which the tape is adhered, and can also provide a measurement of the peel adhesion value of the tape with respect to the selected substrate. The substrate may, for example, be composed of the backsheet film material alone or of the reinforced composite material. When testing a reinforced film composite, the selected adhesive tape is applied to the surface of the film which is opposite to the surface covered by the reinforcement layer. The tape is then peeled from the film at a constant rate with a machine that is capable of measuring the peel force of the tape. If the tape is peeled from the film without stretching or tearing the film, the mean peel force is recorded. If the film stretches, tears or delaminates from the reinforcement coating, the failure mode is noted and the peel value is recorded.

Figure 4:
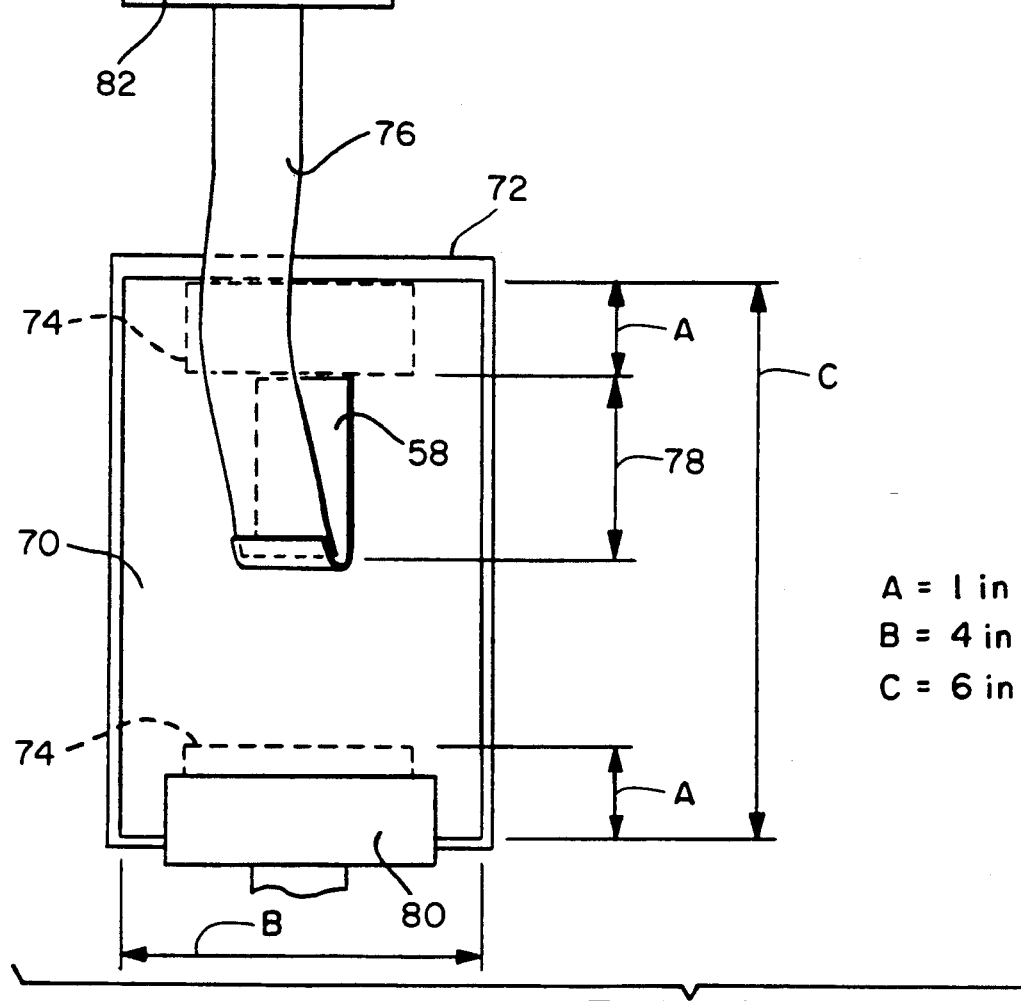
FIG. 4 representatively shows a test specimen for comparing the peel adhesion value of a fastening tape relative to a selected substrate material.

With reference to FIG. 4, the tape refastenability test procedure employs a test specimen 70 measuring 4 inch×6 inch with the 6 inch dimension running in the longitudinal direction, along which the testing force is applied. The test specimen is anchored to a 6 inch×4 inch×1/16 inch stainless steel plate 72 by adhering the 4 inch wide ends of the test specimen with a suitable, high strength, double-sided adhesive tape 74. The double-sided tape is 1 inch wide and 2–2.5 inch long, and has sufficient adhesive strength to secure the ends of the test specimen to the steel plate during the course of the test. The double-sided tape is located between the test specimen and the steel plate, and the adhesion is produced by rolling over the composite with a 4.5 lb, 1.75 inch wide, rubber covered roller. The roller is rolled over the double sided tape region 2 times at a rate of 1 ft/min.

When securing the test specimen to the steel plate, the specimen should be dragged or draped into position to minimize wrinkling or stretching of the specimen.

A 1 inch×8 inch leader strip 76 composed of a material sufficiently strong to withstand the stresses of this test without breaking, such as brown kraft wrapping paper, is connected to a piece of test tape 58 with an overlap of approximately 0.25 inches. The test tape is then adhered to test specimen 70 as illustrated in FIG. 4 to provide a standard gauge length 78 which measures 1 inch. The test specimen is then placed in the jaws of a suitable high speed tensile testing machine, such as a Model 318 high speed tensile tester marketed by MTS, Inc. of Minneapolis, Minn. As illustrated in FIG. 4, the lower machine jaws 80 clamp the portions of the steel plate and the test specimen which are adhered together by the double-sided tape. The upper machine jaws 82 attach to the end of the leader strip. The machine settings are a crosshead speed of 420 in/min or other desired crosshead speed; a jaw separation of 4 inches; and a full-scale load of 2000 gm. The test tape is then pulled back on itself with the test machine to peel the test tape away from the film substrate at a 180° peel angle. Data processing equipment within the MTS instrument can be employed to record and display the average peel load in grams. The test is performed in a standard conditioning atmosphere of 50%, plus or minus 2%, relative humidity and 23° C., plus or minus 1° C., temperature.

The tape refastenability test may be varied to increase the sensitivity of the test. In the standard test, the testing tape has an average peel strength of about 500 gm/in of tape width, and the gauge length is 1 inch. To increase the severity and sensitivity of the test, the average peel strength of the testing tape can be increased to about 700 gm/in, or the test gauge length may be increased to 2 inches, or both.

Adhesive layers, such as layers or patterns of hot melt construction adhesive, have been employed to strengthen the backsheet against tearing. Such adhesives, however, have typically been configured to provide relatively low amounts of elongation. As a result, the adhesives have not been able to sufficiently elongate to accommodate the stretching and strain imparted to the backsheet when the tape tab is rapidly peeled therefrom. Consequently, the reinforcement layer can crack and fracture, and can lose its ability to adequately reinforce the backsheet material.

In contrast to conventional structures, the configuration of the present invention can advantageously provide a reinforcement layer which sufficiently stretches and elongates to reduce fracturing when subjected to the strains induced by peeling tape tab 40 from adhesive contact with the overlying, laminated backsheet layer 12. In a particular aspect of the invention, reinforcement layer 50 is capable of providing an elongation-at-break of at least about 100% when subjected to a strain rate of at least about 0.26 cm/cm/sec.

When reinforcement layer 50 is coated or otherwise applied and attached to backsheet 12, the resultant reinforced composite 60 has a tensile strength sufficient to withstand the stresses and strains generated by peeling tape tab 40 from adhesive contact with backsheet 12. More particularly, the reinforced composite has a yield tensile strength of at least about 5.17 MPa (about 750 psi), and preferably, has a yield tensile strength of at least about 5.52 MPa (about 800 psi) to provide improved performance. In addition, reinforced composite 60 is capable of providing a composite elongation-at-break of at least about 100% when subjected to a strain rate of at least about 3 cm/cm/sec, and preferably provides an elongation-at-break of at least about 200% for improved performance.

For the purposes of the present invention, a suitable technique for determining the elongation-at-break of reinforced composite 60 is the following: A selected reinforcement layer material is applied onto an approximately 3.5 inch (about 8.9 cm) wide piece of polyethylene film. The polyethylene film has a thickness of about 0.00125 inch (about 0.0032 cm) and has an ultimate tensile strength of about 16 MPa (2300 psi). A suitable polyethylene film is manufactured by Edison Thermoplastics located in South Plainfield, N.J. The reinforcement layer material is applied to form a coating, which measures about 0.004 inches (about 0.01 cm) in thickness and extends substantially continuously over an area having a width of 2 inches (5.08 cm) and a length sufficient to produce the desired number of test samples. A suitable device for applying the coating of reinforcement layer material is a LH1 Acumeter coating machine available from Acumeter Co. located in Marlborough, Mass. The coated polyethylene film is cut along its cross direction into test strips measuring 1 inch (2.54 cm) wide and 3.5 inches (8.9 cm) in length. A 1 inch wide test strip is placed in the grip jaws of a high-speed tensile testing machine with the grip jaws set 1 inch apart. The sample is then elongated at a rate of about 460 cm/min (about 180 inch/min). This elongation rate imparts a strain rate of approximately 3 cm/cm/sec to the test strip. The maximum load and the elongation-at-break sustained by the test strip are then determined employing data obtained from the testing apparatus. The composite was considered to have broken when either the substrate or the reinforcement layer fractured. A suitable testing apparatus is a Model 318 high speed tensile tester manufactured by MTS Incorporated of Minneapolis, Minn. With this device, the cross-head is hydraulically driven and is capable of producing cross-head speeds of up to 1800 inch/min (about 45,700 mm/min) with almost instantaneous acceleration.

In one aspect of the invention, reinforcement layer 50 can be a hot melt adhesive material composed of a blend of ethylene-vinyl acetate (EVA) copolymers, tackifiers and waxes. More particularly, reinforcement layer 50 can be composed of a material consisting essentially of about 5-25% of an ethylene-vinyl acetate copolymer having about 18-40% vinyl acetate and a melt index less than about 100; about 25-45% of an ethylene-vinyl acetate copolymer having about 14-20 wt % vinyl acetate and a melt index greater than about 400; about 30-40 wt % of a tackifying material; and about 10-20 wt % of a paraffin or microcrystalline wax having a needle penetration value of less than about 15 and a melting point within the range of about 70°-100° C. In addition, the composition of the reinforcement layer material may include effective amounts of selected additives, such as antioxidants, to improve processability and stability. It should be understood that the amounts of the selected component materials are determined with the proviso that the components, plus incidental impurities, total 100 wt %.

The material of reinforcement layer 50 contains a distinctive combination of a high molecular weight EVA and a low molecular weight EVA. For the purposes of the present invention, a low molecular weight EVA has a melt index greater than about 400 and has a vinyl acetate content between about 14-20 wt %. A high molecular weight EVA has a melt index less than about 100 and a vinyl acetate content between about 18-40 wt %. A suitable technique for determining the melt index of the EVA copolymers is ASTM 1238-79. A person of ordinary skill should readily understand that molecular weight and melt index are inversely related.

The low molecular weight EVA strengthens the reinforcement layer material while keeping the melt viscosity relatively low. A certain percentage of high molecular weight EVA is incorporated into the material to add toughness, extensibility and shock resistance. Suitable low molecular weight EVAs include, for example, ELVAX 410, ELVAX 310, and ELVAX 210 manufactured by E. I. Du Pont de Nemours Inc.; and UE-647-04 manufactured by United Stated Industrial Chemicals located in New York, N.Y. Suitable high molecular weight EVAs include, for example, ELVAX 260, ELVAX 265, and ELVAX 150 manufactured by duPont DeNemours Inc. and EY-902-35 manufactured by United States Industrial Chemicals. A particularly effective embodiment of the invention includes about 5-25 wt % of the high molecular weight EVA, and about 25-45 wt % of the low molecular weight EVA. For further improved performance, the reinforcement layer material contains about 5-10 wt % of the high molecular weight EVA, and about 40-45 wt % of the low molecular weight EVA.

To improve the effectiveness of the reinforcement layer material, the content of the tackifying material should range from about 30-40 wt %. Too much tackifying resin may create a brittle adhesive, and too little tackifying resin may create a material which is excessively high in viscosity or is excessively brittle, depending on the content of the other constituents.

A low softening point tackifying resin is desirable to decrease the viscosity of the reinforcement layer material. However, the softening point must not be too low because an excessively low softening point may allow the tackifying material to migrate during aging of the reinforcement layer material. Suitable tackifying resins include, for example, Wingtack 95, a polyterpene manufactured by Goodyear; Arkon P70, a hydrogenated polystyrene resin manufactured by Arakawa; Foral 85, a rosin ester manufactured by Hercules Chemical; and Arkon Superester A-100, a rosin ester manufactured by Arakawa.

In a particularly effective embodiment of the invention, the tackifying material is a resin containing a blend of two tackifiers. The first tackifier is a polyterpene or hydrogenated polycyclic or hydrogenated polycyclic hydrocarbon resin having a softening point between about 70°-100° C. The second tackifier is a rosin ester having a softening point between about 70°-100° C. In one aspect of the invention, the polyterpene or hydrogenated polycyclic hydrocarbon resin comprises about 15-35 wt % of the reinforcement material, and the rosin ester comprises about 5-25 wt % of the reinforcement material. In a further aspect of the invention, the polyterpene or hydrogenated polycyclic hydrocarbon resin comprises about 20 wt % of the reinforcement material, and the rosin ester comprises about 15 wt % of the reinforcement material.

The wax component of the reinforcement layer material is employed to lower the viscosity. In addition, the hardness of the wax affects the tensile properties of the reinforcement layer material. In particular, a hard wax can impart a higher modulus and a higher strength to the reinforcement layer composition. For the purposes of the present invention. A suitable technique for determining the wax hardness is a needle penetration test in accordance with ASTM D721. The lower the needle penetration value, the harder the wax. A suitable technique for determining the melting point of the wax is a test in accordance with ASTM D127.

A suitable wax includes, for example, Microwax 163-169 manufactured by International Wax Refining Company, Inc., located in Valley Stream, N.Y. This wax has a needle penetration value of approximately 9 and a melting point of about 74.4° C.

The material of reinforcement layer 50 can be characterized by its tensile properties, including its tensile strength and its elongation-at-break, and can also be characterized by its viscosity. In one aspect of the invention, the reinforcement layer material has a tensile strength, measured at 25% elongation, within the range of about 2-5 MPa (about 300-700 psi), and has a tensile strength-at-yield within the range of about 3-4.5 MPa (about 400-650 psi). In addition, the reinforcement layer material exhibits an elongation-at-yield of at least about 50%, and preferably, of at least about 60%. The reinforcement layer also exhibits an elongation-at-break of at least about 100%, and preferably, of at least about 200%. As a result, the reinforcement layer material can provide sufficient toughness for effectively reinforcing the backsheet layer.

The tensile properties of the reinforcement layer are determined as follows: The reinforcement layer composition is formed into a film measuring $0.003 + 0.001$ inches in thickness, and the film is allowed to stand at room temperature for at least 24 hours. Tensile specimens are then cut with the specimens measuring 1 inch in width and greater than 2 inches in length. The resultant tensile specifications are placed in the jaws of an Instron tensile tester employing a 0.5 inch jaw separation. The test sample is then elongated at a rate of 200 mm/min Data from the tensile tester are employed to determine the tensile stress at 25% elongation, the tensile strength at the yield point, the percent elongation at the yield point and the percent elongation at the breaking point.

To improve its processability, the reinforcement layer composition has a viscosity of less than about 25,000 centipoise (cP), as measured at a shear rate of 1000 sec$^{-1}$ and a temperature of 105° C.

A suitable method for measuring the viscosity of the material is a capillary rheometer viscosity test. A suitable apparatus for this test is a Monsanto Processability Tester (MPT) manufactured by Monsanto, located at Akron, Ohio. This device measures viscosity by forcing the selected material through a capillary with a piston at a selected piston speed. The shear stress is determined by measuring the pressure before the entrance to the capillary, and the viscosity is calculated by dividing the shear stress by the shear rate. It is well understood that the shear rate is readily determined from the piston speed and the capillary diameter. For the purposes of the present invention, the viscosity is measured employing a capillary having 1 mm diameter and 30 mm length. In addition, the piston speed of the MPT apparatus is set at 2.08 cm/sec (0.82 in/sec) to produce a shear rate of 1000 sec$^{-1}$.

The following examples are given to provide a more detailed understanding of the invention. The particular components, amounts, proportions and parameters are exemplary, and are not intended to specifically limit the scope of the present invention.

EXAMPLE 1

30 grams of white Microwax 163/169 from International Wax Company was melted in a heated flask, and 1 gram of Ethanox 702 antioxidant was added. This antioxidant is available from Ethyl Co., located in Baton Rouge, La. 35 grams of Arkon P-70 and 35 grams of Arkon Superester A100 tackifiers from Arakawa Chemical Co. were slowly stirred into the melted wax. Next, 60 grams of ELVAX 410 EVA polymer from Du Pont and 40 grams of EY-902-35 EVA resin from United States Industrial Chemical Co. were slowly added to the mixture at about 150° C. The resulting adhesive composition, S1, was tested for tensile properties employing the thin film tensile test and was checked for viscosity at 105° C. employing the Monsanto Processability Tester. The material exhibited the properties set forth in Table 1 below.

TABLE 1

| S1 | | | |
|---|---|---|---|
| Tensile Strength | | Elongation | Viscosity |
| At 25% elong. | At yield | At yield / At break | At 1000 sec$^{-1}$ |
| 113 psi | 366 psi | 121% / 250% | 19,000 cP |

EXAMPLE 2

The following formulation, S2, exhibited increased strength and lower elongation properties. The components were mixed in the manner set forth in Example 1 with the following proportions: 43 wt % ELVAX 410 EVA polymer; 7 wt % ELVAX 265 EVA polymer; 15 wt % International White Microwax 163/169; 20 wt % ARKON P70 tackifying resin; 15 wt % Arkon Superester A-100 tackifying resin; and 1 pph Irganox 1010 antioxidant, available from Ciba Geigy Co., located in Ardsley, N.Y. The resultant material exhibited the properties set forth in Table 2 below.

TABLE 2

| S2 | | | |
|---|---|---|---|
| Tensile Strength | | Elongation | Viscosity |
| At 25% elong. | At yield | At yield / At break | At 1000 sec$^{-1}$ |
| 390 psi | 450 psi | 50% / 100% | 22,000 cP |

EXAMPLE 3

The following sample formulation, S3, was prepared with the ingredients set forth in Table 3A below and had the properties set forth in Table 3B below.

TABLE 3A

| S3 | |
|---|---|
| INGREDIENTS | wt % |
| Elvax 410 | 55.0 |
| Microwax (175° F.) (soft) | 12.5 |
| Microwax (163/169° F.) (hard) | 12.5 |

TABLE 3A-continued

| S3 | |
|---|---|
| INGREDIENTS | wt % |
| Arkon M-100 | 20.0 |

TABLE 3B

| S3 | |
|---|---|
| PROPERTIES | |
| Viscosity @ 230° F. | 13,700 cP |
| Young's Modulus | 5,200 psi |
| Yield Tensile Strength (ASTM D-638) | 572 psi |
| Elongation at yield (ASTM D-638) | 70% |

A reinforced composite prepared with this formulation was not acceptable since the formulation would crack when aged at 130° F. for two days.

EXAMPLES 4-7

The following sample formulations were prepared. The formulations had the ingredients and the properties set forth in Table 4 below. Sample S5 is essentially the same as S1.

TABLE 4

| | S4 | S5 | FINDLEY H-1002-03 | FINDLEY 295 |
|---|---|---|---|---|
| INGREDIENTS | | | | |
| Elvax 410 (18% VA) | 30 | 30 | | |
| USI EY902-35 (41% VA) | 15 | 20 | | |
| Microwax (163/169° F.) | 15 | 15 | | |
| Escorez 5380 | 40 | — | | |
| Arkon P-70 | — | 17.5 | | |
| Superester A-100 (rosin ester) | — | 17.5 | | |
| PHYSICAL PROPERTIES | | | | |
| Tensile (psi) (@ 25% elong.) | 114 | 113 | 289 | 238 |
| Tensile (psi) (@ yield) | 413 | 366 | 664 | — |
| Elongation (%) (@ yield) | 287 | 121 | 112 | — |
| Ultimate Tensile (psi) | 400 | 436 | 736 | 543 |
| Ultimate Elongation (%) | 400 | 725 | 658 | 100 |

Escorez 5380 is a tackifier manufactured and distributed by Exxon Corp. of Houston, Tex. The Findley formulations were prepared and provided by Findley Adhesives Co. of Milwaukee, Wis.

The Findley 295 formulation produced an offensive odor during processing, and the Findley H-1002-03 formulation exhibited unacceptable aging characteristics. In particular, when the latter formulation was coated onto a conventional polyethylene backsheet material and the composite aged at 130° F. for three days, the adhesion of a standard tape tab against the backsheet was unacceptably reduced.

EXAMPLES 8-15

The following sample formulations were prepared. The formulations had the ingredients set forth in Table 5 below and had the properties set forth in Table 6 below. The tensile values shown in Table 6 were obtained from thin-film samples of the formulations. These tensile values changed from test to test. The reported values are normalized values based on how much sample S7 changed from test to test.

TABLE 5

| Base Polymer (wt. %) | Wax (wt %) | Tackifier (wt %) |
|---|---|---|
| Sample S6 | | |
| 30.0 USI EY-649-04  20.0 USI EY-902-35 | 15.0 Int. White 163/169 | 10.0 Escorez 5380  15.0 Arkon P70  10.0 Kristalex 3085 |
| Sample S7 | | |
| 30.0 USI UE 649-04  20.0 USI EY-902-35 | 15.0 Int. White 163/169 | 15.0 Arkon Superester A100  20.0 Arkon P-70 |
| Sample S8 | | |
| 30.0 USI UE 649-04  20.0 Elvax 150 | 15.0 Int. White 163/169 | 10.0 Escorez 5380  15.0 Arkon P-70  10.0 Kristalex 3085 |
| Sample S9 | | |
| 30.0 USI UE 647-04  20.0 Elvax 450 | 15.0 Int. White 163/169 | 10.0 Escorez 5380  15.0 Arkon P-70  10.0 Kristalex 3085 |
| Sample S10 | | |
| 40.0 USI UE 649-04  10.0 Elvax 265 | 15.0 Int. White 163/169 | 10.0 Escorez 5380  15.0 Arkon P-70  10.0 Kristalex 3085 |
| Sample S11 | | |
| 30.0 USI UE649-04  20.0 70/30 Elvax 250/230 | 15.0 Int. White 163/169 | 10.0 Escorez 5380  15.0 Arkon P-70  10.0 Kristalex 3085 |
| Sample S12 | | |
| 43.0 USI UE 649-04  7.0 Elvax 265 | 15.0 Int. White 163/169 | 15.0 Arkon Superester A100  20.0 Arkon P-70 |
| Sample S2 | | |
| 43.0 Elvax 410  7.0 Elvax 265 | 15.0 Int. White 163/169 | 15.0 Arkon Superester A100  20.0 Arkon P-70 |

Kristalex 3085 is a poly alpha-methylstyrene tackifier resin manufactured and distributed by Hercules of Wilmington, Del.

TABLE 6

| TENSILE STRENGTH (PSI) AT 25% ELONGATION | TENSILE STRENGTH AT YIELD (PSI) | ELONGATION AT YIELD (%) | ELONGATION AT BREAK (%) |
|---|---|---|---|
| Formulation S6 | | | |
| 320 | 380 | 60 | 400 |
| Formulation S7 | | | |
| 310 | 370 | 60 | 300 |
| Formulation S8 | | | |
| 370 | 430 | 60 | 210 |
| Formulation S9 | | | |
| 500 | 570 | 60 | 230 |
| Formulation S10 | | | |
| 430 | 490 | 60 | 140 |
| Formulation S11 | | | |
| 390 | 440 | 60 | 340 |
| Formulation S12 | | | |
| 400 | 480 | 50 | 430 |
| Formulation S2 | | | |
| 390 | 450 | 50 | 100 |

Sample S2 corresponds to the similarly identified samples set forth in Example 2 above.

An increase of the tensile strength was observed as one lowered the vinyl-acetate content of EVA polymers in the formulations.

EXAMPLES 16-22

The results of aging studies performed on reinforced composites are shown in Table 7.

TABLE 7

Composite Aging Studies

| FORMULATION | DEGREE OF CRACKING AFTER 3 DAYS AT 130° F. | DEGREE OF CRACKING AFTER 6 DAYS AT 130° F. |
|---|---|---|
| S6 | Severe | |
| S7 | Slight to none | Slight |
| S8 | Slight to none | Slight |
| S10 | None | Slight |
| S11 | Slight | Severe |
| S12 | None | Moderate |
| S2 | None | None |

Comparison of the aging results between S6 and S7 indicated that Arkon Superester A100 had a better compatibility in the formulation than a combination of Kristalex and Escorez resins. Comparison of the results between S12 and S2 indicated that Elvax 410 had a better aging stability than UE 649-04. It is not understood why the aging results for S11 were worse than those for S10 and S8. It was found, however, that formulations containing Elvax 410 and Arkon Superester A100 had the best aging stability.

EXAMPLE 23

Tensile tests were performed to evaluate the ability of composites to withstand high strain rates. Results are summarized in Table 8 below. The test specimens employed for Table 8 had a polyethylene film thickness of 0.0017 inches, a reinforcement coating thickness of 0.004 inches, and a width of 1 inch. As a result, the reinforced composite film had a total thickness of 0.0057 inches and a cross-sectional area of 0.0057 (inch)$^2$.

TABLE 8

MTS Tensile Results on Coated Composites

| TEST SPEED (mm/min.) | HOT MELT COATING FORMULATION | PEAK LOAD (g) | BREAK ELONG. (%) |
|---|---|---|---|
| 4500 | S7 | 2026 ± 105 | 347 ± 10 |
| | S8 | 2079 ± 48 | 343 ± 4 |
| | S10 | 2259 ± 92 | 307 ± 77 |
| | S11 | 2096 ± 44 | 336 ± 15 |
| | S12 | 2289 ± 67 | 191 ± 47 |
| | S2 | 2131 ± 11 | 323 ± 60 |
| | Findley H100203 | 2631 ± 63 | 201 ± 127 |
| 45,000 | S8 | 4292 ± 270 | 268 ± 67 |

TABLE 8-continued

| | MTS Tensile Results on Coated Composites | | |
|---|---|---|---|
| TEST SPEED (mm/min.) | HOT MELT COATING FORMULATION | PEAK LOAD (g) | BREAK ELONG. (%) |
| | S10 | 4493 ± 403 | 159 ± 99 |
| | S11 | 3948 ± 510 | 285 ± 74 |
| | S2 | 4954 ± 572 | 278 ± 60 |
| | Findley H100203 | 5576 ± 349 | 94 ± 10 |

Tensile tests at a strain rate 4500 mm/min. demonstratead the differences in tensile properties between S12 and S2. Differences between S12 and S2 were also seen in aging studies shown in Table 7; S2 being better than S12. Referring to Table 5, the differences in formulations between S12 and S2 are the EVA polymers: Elvax 410 for S2, and UE 649-04 for S12. Both EVA polymers had the same vinyl acetate contents and melt indexes. The results shown in Tables 7 and 8 indicated subtle differences in both polymers; Elvax 410 had better compatibility with the rest of the composition than UE647-04.

EXAMPLE 24

To compare the composite toughness of formulation S2 with two Findley's formulations, H1013X and H1014X, five composite samples employing each hot melt were tested for frequency of break when elongated over a four inch composite sample at 45,000 mm/min. The results shown in Table 9 indicated that formulations of the invention are more ductile and therefore tougher than the two Findley formulations.

TABLE 9

| Composite Toughness Comparison In-House Formulations vs. Findley's Submission Four Inches Span at 1800 Inches/Min. | |
|---|---|
| HOT MELTS | NUMBER OF SPECIMEN THAT BROKE OUT OF FIVE |
| S2 | 2/5 |
| Findley H1013X | 5/5 |
| Findley H1014X | 5/5 |

Having thus described the invention in rather full detail, it will be readily appreciated the various changes and modifications can be made without departing from the spirit of the invention. All of such changes and modifications are contemplated as being within the scope of the invention, as defined by the subjoined claims.

We claim:

1. An article, comprising:
   a. a flexible substrate having a tear strength;
   b. an adhesive tape member having a peel adhesion value which is greater than the tear strength of said substrate, said peel adhesion value determined with respect to a first major surface of said substrate to which said tape member is to be adhered;
   c. A reinforcement layer which is composed of a hot melt adhesive and is bonded to a second major surface of said substrate located opposite to said first major surface, said reinforcement layer exhibiting an elongation-at-break of at least about 100% and a tensile strength, measured at 25% elongation, which is within the range of about 2-5 MPa (about 300-700 psi);
   d. said substrate and said reinforcement layer thereby providing a composite tear strength greater than the peel adhesion value of said tape member and providing a composite elongation-at-break of at least about 100%, as measured at a strain rate of 3 cm/cm/sec.

2. An absorbent article, comprising:
   a. a flexible, liquid impermeable backsheet having a tear strength and defining a front waistband portion, a back waistband portion and an intermediate portion interconnecting said front and back waistband portions;
   b. a liquid permeable topsheet located in facing relation with said backsheet;
   c. an absorbent body located between said backsheet and said topsheet;
   d. an adhesive tape member connected to each of two side sections of said back waistband portion of the backsheet, said tape member having a peel adhesion value which is greater than the tear strength of said backsheet to a first major surface of said backsheet, said peel adhesion value determined with respect to a first major surface of said backsheet to which said tape member is to be adhered; and
   e. a reinforcement layer which is composed of a hot melt adhesive bonded to a second major surface of said backsheet located opposite to said first major surface, said reinforcement layer exhibiting an elongation-at-break of at least about 100% and a tensile strength, measured at 25% elongation, which is within the range of about 2-5 MPa (about 300-700 psi);
   f. said backsheet and said reinforcement layer thereby providing a composite tear strength greater than the peel adhesion value of said tape member and providing a composite elongation at break of at least about 100%, as measured at a strain rate of 3 cm/cm/sec.

3. An article, comprising:
   a. a flexible substrate having a tear strength;
   b. an adhesive tape member having a peel adhesion value which is greater than the tear strength of said substrate, said peel adhesion value determined with respect to a first major surface of said substrate to which said tape member is to be adhered; and
   c. a reinforcement layer attached to a second major surface of said substrate located opposite said first major surface, said reinforcement layer composed of a material consisting essentially of
      (i) about 5-25 wt % of a first ethylene-vinyl acetate copolymer containing about 18-40 wt % vinyl acetate and having a melt index of less than about 100,
      (ii) about 25-45 wt % of a second ethylene-vinyl acetate copolymer containing about 14-20 wt % vinyl acetate and having a melt index of greater than about 400,
      (iii) about 30-40 wt % of tackifier material, and
      (iv) about 10-20 wt % of a paraffin or microcrystalline wax having a needle penetration value of less than about 15 and having a melting point within a temperature range of about 70°-100° C., with the proviso that the component materials, plus incidental impurities, total 100 wt %;
   d. said substrate and said reinforcement layer thereby providing a composite tear strength greater than said peel adhesion value of said tape member.

4. An article as recited in claim 3, wherein said reinforcement layer material includes about 5-10 wt % of said first ethylene-vinyl acetate copolymer and about 40-45 wt % of said second ethylene-vinyl acetate copolymer.

5. An article as recited in claim 4, wherein said reinforcement layer includes about 7 wt % of said first ethylene-vinyl acetate copolymer and about 43 wt % of said second ethylene-vinyl acetate copolymer.

6. An article as recited in claim 3, wherein said tackifier material consists essentially of:
   a. a polyterpene or hydrogenated polycyclic hydrocarbon resin having a softening point between about 70°-100° C.; and
   b. a rosin ester having a softening point between about 70°-100° C.

7. An article as recited in claim 6, wherein said polyterpene or hydrogenated polycyclic hydrocarbon resin comprises about 15-35 wt % of said reinforcement material, and said rosin ester comprises about 5-25 wt % of said reinforcement material.

8. An article as recited in claim 6, wherein said polyterpene or hydrogenated polycyclic hydrocarbon resin comprises about 20 wt % of said reinforcement material, and said rosin ester comprises about 15 wt % of said reinforcement material.

9. An article as recited in claim 3, wherein said reinforcement layer exhibits an elongation-at-break of at least about 100%.

10. An article as recited in claim 3, wherein said substrate and said reinforcement layer provide a composite elongation-at-break of at least about 100%.

11. An absorbent article, comprising:
   a. a flexible, liquid impermeable backsheet having a tear strength and defining a front waistband portion, a back waistband portion and an intermediate portion interconnecting said front and back waistband portions;
   b. a liquid permeable topsheet located in facing relation with said backsheet;
   c. An absorbent body located between said backsheet and topsheet;
   d. an adhesive tape member connected to each of two side sections of said back waistband portion of the backsheet, said tape member having a peel adhesion value which is greater than the tear strength of said substrate, said peel adhesion value determined with respect to a first major surface of said backsheet to which said tape member is to be adhered; and
   e. a reinforcement layer attached to a second major surface of said backsheet located opposite said first major surface, said reinforcement layer composed of a material consisting essentially of,
      (i) about 5-25 wt % of a first ethylene-vinyl acetate copolymer containing about 18-40 wt % vinyl acetate and having a melt index of less than about 100,
      (ii) about 25-45 wt % of a second ethylene-vinyl acetate copolymer containing about 14-20 wt % vinyl acetate and having a melt index of greater than about 400,
      (iii) about 30-40 wt % of a tackifier material, and
      (iv) about 10-20 wt % of a paraffin or microcrystalline wax having a needle penetration value of less than about 15 and having a melting point within a temperature range of about 70°-100° C., with the proviso that the component materials, plus incidental impurities, total 100 wt %;
   f. said backsheet and said reinforcement layer thereby providing a composite tear strength greater than said peel adhesion value of said tape member.

12. An article as recited in claim 11, wherein said reinforcement layer material includes about 5-10 wt % of said first ethylene-vinyl acetate copolymer and about 40-45 wt % of said second ethylene-vinyl acetate copolymer.

13. An article as recited in claim 12, wherein said reinforcement layer includes about 7 wt % of said first ethylene-vinyl acetate copolymer and about 43 wt % of said second ethylene-vinyl acetate copolymer.

14. An article as recited in claim 11, wherein said tackifier material consists essentially of:
   a. a polyterpene or hydrogenated polycyclic hydrocarbon resin having a softening point between about 70°-100° C.; and
   b. a rosin ester having a softening point between about 70°-100° C.

15. An article as recited in claim 14, wherein said polyterpene or hydrogenated polycyclic hydrocarbon resin comprises about 20 25 % of said reinforcement material, and said rosin ester comprises about 15 wt % of said reinforcement material.

16. An article as recited in claim 11, wherein said reinforcement layer exhibits an elongation-at-break of at least about 100%.

17. An article as recited in claim 11, wherein said substrate and said reinforcement layer provide a composite elongation-at-break of at least about 100%.

18. An article as recited in claim 1, wherein said reinforcement layer exhibits a tensile strength, measured at 25% elongation, which is within the range of about 3-4.5 MPa (about 400-650 psi).

19. An article as recited in claim 11, wherein said reinforcement layer exhibits a tensile strength, measured at 25% elongation, which is within the range of about 2-5 MPa (about 300-700 psi).

20. An article as recited in claim 11, wherein said reinforcement layer exhibits a tensile strength, measured at 25% elongation, which is within the range of about 3-4.5 MPa (about 400-650 psi).

* * * * *